United States Patent [19]

Pollock et al.

[11] Patent Number: 4,618,489

[45] Date of Patent: Oct. 21, 1986

[54] DENTAL COMPOSITIONS AND METHOD OF USE THEREFOR

[75] Inventors: Jerry J. Pollock, East Setauket; Thomas F. McNamara, Port Jefferson, both of N.Y.

[73] Assignee: Research Foundation of the State University of New York, Albany, N.Y.

[21] Appl. No.: 529,163

[22] Filed: Sep. 2, 1983

[51] Int. Cl.[4] .......................... A61K 9/16; A61K 9/18
[52] U.S. Cl. ........................................ 424/52; 424/49
[58] Field of Search ...................... 424/48, 49, 50, 94, 424/129, 153, 151, 52

[56] References Cited

U.S. PATENT DOCUMENTS

| | | | |
|---|---|---|---|
| 1,169,998 | 2/1916 | Rhodes | 424/49 |
| 2,024,146 | 12/1935 | Crowther | 424/49 |
| 2,128,917 | 9/1938 | Crocker | 424/49 |
| 2,658,851 | 11/1953 | Brandenberger et al. | 424/49 |
| 2,994,642 | 8/1961 | Bossard | 424/49 |
| 3,590,120 | 6/1971 | Muhler | 424/48 |
| 3,689,636 | 9/1972 | Svajda | 424/49 |
| 3,761,583 | 9/1973 | Gladstone | 424/48 |
| 3,937,804 | 2/1976 | Delaney et al. | 424/52 |
| 3,975,514 | 8/1976 | Weisz | 424/52 |
| 4,024,237 | 5/1977 | Eichel et al. | 424/49 |
| 4,150,113 | 4/1979 | Hoogendoorn et al. | 424/48 |
| 4,150,151 | 4/1979 | Pader et al. | 424/49 |
| 4,178,362 | 12/1979 | Hoogendoorn et al. | 424/94 |
| 4,269,822 | 5/1981 | Pellico et al. | 424/94 |
| 4,327,079 | 4/1982 | Aoki | 424/49 |
| 4,367,218 | 1/1983 | Jacobson | 424/49 |

FOREIGN PATENT DOCUMENTS

| | | | |
|---|---|---|---|
| 2043279 | 3/1972 | Fed. Rep. of Germany | 424/48 |
| 376604 | 7/1932 | United Kingdom | 424/49 |
| 900389 | 7/1962 | United Kingdom | 424/48 |

Primary Examiner—Shep K. Rose
Attorney, Agent, or Firm—Omri M. Behr

[57] ABSTRACT

Dental compositions containing bicarbonate anion in combination with a monovalent anion such as fluoride, chloride or thiocyanate and methods of using them in anti-caries therapy are disclosed herein.

5 Claims, 14 Drawing Figures

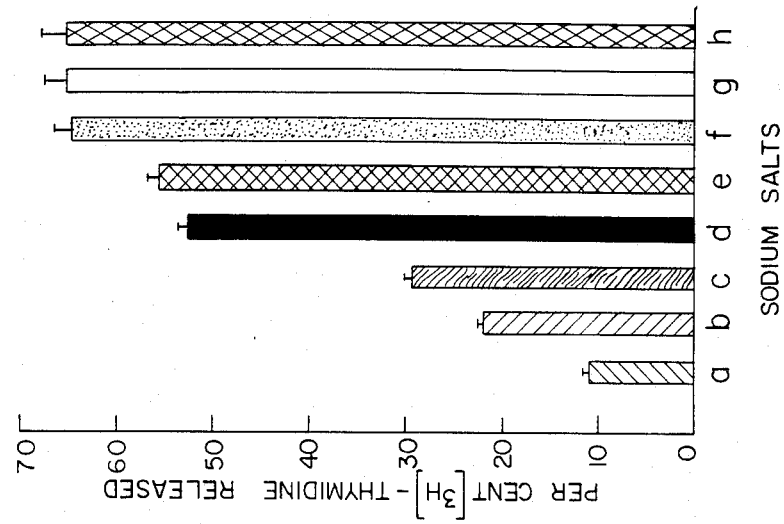
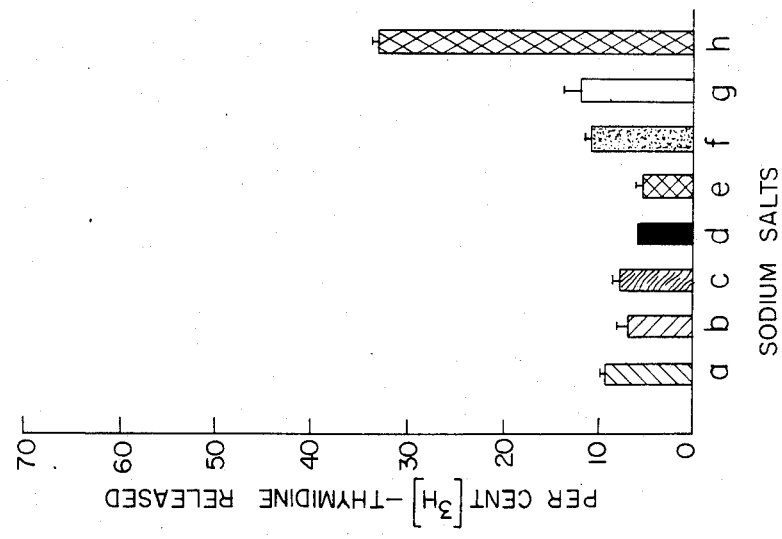

DENTAL COMPOSITIONS AND METHOD OF USE THEREFOR

BACKGROUND OF THE INVENTION

Prevention is recognized as the most important ingredient of good dental care. Cavities are now recognized to be of bacterial origin; bacteria in the mouth combine with sugars, remaining on or between the teeth to produce acid that destroys tooth enamel and eats into the heart of the tooth. Limiting the amount of ingested sugar can reduce the incidence of cavities. Unfortunately, such self limitation in most population groups usually remains modest and is easily reversible. For this reason automatic caries-preventive measures such as fluoridated water, fluoride toothpastes and rinses and fluoride-supplemented vitamins and foodstuffs have been developed.

Studies have shown that marked caries reduction can be obtained by bicarbonate-phosphate or bicarbonate-phosphate-fluoride combinations mixed into the dietary sugar of rats. (Luoma, et. al., *Caries Res.*, 4, pp. 332–346 (1970)). Other studies in a controlled population of institutionalized mentally handicapped children have shown that the inclusion of fluoride and a bicarbonate-phosphate mixture in sweet sugar products of the children's diet produces caries arrestment after the first year. (Luoma, et. al., *Scand. J. Dent. Res.*, 87, pp. 197–207 (1979). In these studies, Luoma added the bicarbonate fraction mainly to serve as the buffering agent while the phosphate component (a divalent anion) was added to satisfy the phosphate need of cariogenic bacteria in order to prevent the enamel phosphate from being utilized for the bacteria's metabolic need.

Both thiocyanate and chloride anions have recognized roles in lactoperoxidase and myeloperoxidase antibacterial systems (Jago and Morrison, *Proc. Soc. Exp. Biol. Med.*, 111, pp 585–588 (1962); Zeldow, *J. Immunol.*, 90, pp. 12–16 (1963); and Klebanoff, *J. Bacteriol.*, 95, pp 2131–2138 (1968)).

The antibacterial effects of fluoride have been known for many years (Bibby and VanKesteren, *J. Dent. Res.*, 19, pp. 391–402 (1940)) and bicarbonate has been proposed to stabalize the iron binding properties of human milk lacteroferrin (Masson and Hermens, *Eur. J. Biochem.*, 6, pp. 579–584 (1968)).

The concentrations of each of these anions have been observed to vary with salivary flow rate and with duration of collection at fixed flow rates. (Dawes, *Archs. Oral. Biol.* 14, 277 (1969); Jenkins, "The Physiology and Biochemistry of the Mouth", 4th ed, pp. 284–359 (1978); Kreusser, et. al., *Eur. J. Clin. Invest.*, 2, pp 398–406, (1972). Natural, normal physiological concentrations in submandibular parotid and mixed human salivas range for bicarbonate from about 1–60 mM, for chloride from 10 to 50 mM and thiocyanate from 0.5 to 4.5 mM (Jenkins, supra). After a mouth rinse for two minutes with 0.2% sodium fluoride, salivary fluoride concentrations were found to average 36 millimolar (Bruun, et. al., *Communits. Dent. Oral. Epidemiol.*, 10, pp. 174–129 (1982)). These concentrations, naturally occurring or otherwise, are ineffective individually to lyse and therefore kill caries bacteria. It has now been found that compositions containing bicarbonate anion and a monovalent anion act synergistically so that compositions together containing a subeffective amount of both the bicarbonate anion and the monovalent anion are effective agents for anti-caries therapy.

SUMMARY OF THE INVENTION

The present invention relates to compositions adapted for treating and inhibiting dental caries which comprises 10–120 millimolar bicarbonate anion, and
20–100 millimolar of a monovalent anion, or mixtures thereof, in a vehicle suitable for oral or oral cavity administration, said composition being substantially free of divalent anions. This invention also relates to a method of using such compositions for treating and inhibiting dental caries in mammals, particularly humans, in need of anti-caries therapy.

In particular, the invention comprises enhancing the ability of enzymes such as lysozyme, trypsin and chymotrypsin, either individually or in combination (as they usually are found in the oral cavity) to lyse cariogenic bacteria, such as *Streptococcus mutans*, *Lactobacillus casei*, *Actinomyces viscosus* and *Actinomyces naeslundii*. This list of lysable microorganisms is not considered exhaustive merely illustrative.

The monovalent anion utilized in the compositions of the present invention may suitably, be the fluoride, chloride or thiocyanate anion, or any physiological equivalent thereof or mixtures thereof. The anion can be formulated in the composition in the form of its potassium, sodium, calcium or other non-toxic, pharmacologically acceptable salt. Particularly preferred for purposes of this invention is the sodium salt of the monovalent anion.

The bicarbonate anion utilized in the compositions of the present invention can likewise be utilized in the form of potassium, sodium, calcium or other non-toxic, pharmacologically acceptable salt. For ease of formulation in the present invention, the sodium salt is preferred.

Amounts of the monovalent anion utilized in the compositions of the present invention range from 20–100 millimolar, with a range of 30–60 millimolar being generally used.

The bicarbonate anion is utilized in the compositions of the present invention in an amount of about 10–120 millimolar with a range of about 30–80 millimolar being generally preferred.

The compositions of the present invention are conventionally formulated into the commonly utilized dental treatment agents, i.e., dentifrices, mouthwashes and toothpastes, as well as into typically chewed carriers such as gum, candies and vitamins. For instance, the fluoride anion, commonly incorporated into dentifrices, mouthwashes, toothpastes and vitamins can be incorporated at similar lower levels with greater effectiveness by virtue of the present invention.

The method of utilizing the compositions of the present invention involves treatment of mammals, particularly humans, in need of anti-caries therapy with an anti-caries effective amount of the compositions of the present invention. Obviously, the anti-caries effective amount will vary slightly with the particular formulation utilized. Typically, the composition will be administered from one to three times daily.

While it has been found effective to enhance the enzymatic lysis of cariogenic bacteria in the situs of the oral cavity, the invention is not limited to the enhancement of the lytic process of these bacteria in that location.

The synergistic properties of the compositions of the present invention are determined by standardized assay procedures involving the bacteriolysis of *Streptococcus mutans* GS 5. The lysis is assayed by release of tritiated thymidine. The percentage of lysis is indicative of the ability of the composition to destroy the decay-causing microorganisms in the oral cavity.

BRIEF DESCRIPTION OF THE DRAWINGS

FIGS. 6 (A & B) are bar graphs of the lysis obtained with sublytic concentrations of bicarbonate anion and combinations with fluoride, chloride and thiocyanate.

EXAMPLES

Figure 1A:
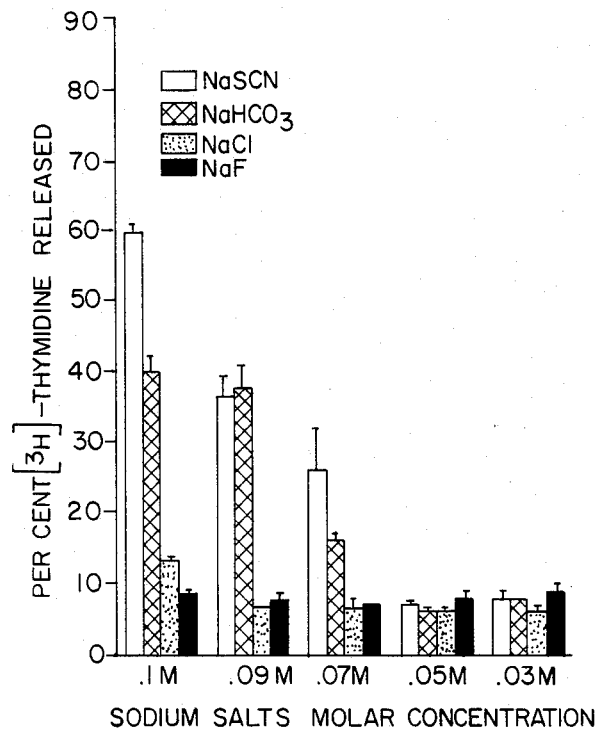
FIGS. 1 (A-D) is a set of Bar graphs showing thymidine release (lysis) at various single anion concentrations with varying enzyme concentrations.

The materials and method of the assay are as follows:

Chemicals

All chemicals are of the highest purity available. Sodium Chloride (biological grade), sodium thiocyanate (ACS grade), sodium bicarbonate (ACS grade), sodium acetate and acetic acid are obtained from Fisher (Springfield, N.J.). Sodium fluoride (analaytical grade) is obtained from Baker (Phillipsburg, N.J.). HEPES (N-2-hydroxyethylpiperazine-N-2-ethane sulfonic acid) (ultrol grade) and MES (2-N-morpholino)ethane sulfonic acid) are obtained from Calbiochem (La Jolla, Calif.). (Methyl-$^3$H)-thymidine is a product of ICN Pharmaceuticals (Irvine, Calif.). NCS is obtained from Amersham Corp. (Arlington Heights, Ill.) and Soluscint O from National Diagnostics (Somerville, N.J.). Hen egg white lysozyme (HEWL, 3× crystallized), trypsin (bovine pancreas, type III) and alpha chymotrypsin (Type II, 3× crystallized) are obtained from Sigma Chemical Co. (St. Louis, Mo.). The concentration of HEWL is determined from the extinction coefficient of $E_1$ $_{cm}$$^{1\%}$=26.9 (Kuramitsu, et al., *J. Biochem.* (Tokyo 78, pp. 327-333, (1975)).

Bacterial Cultures

*Strep. mutans* GS5 is obtained from Dr. Harols Jordan (Fortyth Dental Center, Boston). Stock cultures grown to late exponential phase in brain heart infusion (BHI) broth (Difco Laboratories, Detroit, Mich.) are stored quick-frozen at −90° C. in 1% skim milk. During the course of these experiments, it became necessary to freeze-down a second batch of cultures. For routine use, freshly grown cells are inoculated as either 1:10,000 or 1:100,000 dilutions in FMC synthetic media (10 ml) supplemented with NaHCO$_3$ (0.01M final concentration) (Terleckyj, Willett and Shockman, *Infect. Immun.*, 11, pp 649-655 (1975)) and 10 uCi/ml (methyl-$^3$H)-thymidine (sp. act. 1 mCi/ml, 20 Ci/mmole) (Pollock, et. al., *Archs. Oral. Biol.*, 26, pp 711-716 (1981)). Bacteria are harvested in the log phase of growth (optical density 0.68 at 675 nm) and washed three times in ice-cold distilled water. Cells are then resuspended in buffers of selected pH and an ionic strength of 0.025 to an optical density at 700 nm of 0.20 (5.6×10$^8$ cells/ml, Petroff-Hausser bacterial chamber) immediately prior to lytic assays.

Assays

Lysis is assayed by release of tritiated thymidine from *Strep. mutans* GS5 as previously described (Pollock et. al., *Arch. Oral Biol.*, 26, pp. 711-716 (1981); Goodman, et. al., *J. Bacteriol.*, 146, pp. 764-774 (1981)).

The effects of bicarbonate on lysis is determined by experiments conducted in either MES buffer, pH 5.2, or acetate buffer, pH 4.0 ($^3$H)-thymidine. Suspensions are first preincubated for 1 hour with stirring at 37° C. after which cells were treated with trypsin (75 ug/ml), lysozyme (30 ug/ml) or a combination of HEWL plus trypsin. After 2 hours incubation with the enzymes, varying concentratons of sodium bicarbonate (0.01 to 0.15M final molarity) are added, the pH immediately recorded and the cells further incubated with a bicarbonate for an additional 2 hour period. At this time, 1 ml samples are removed, blended in a Vortex mixer and processed for DNA release (Goodman et al., *J. Bacteriol.*, 146, 764-774 (1981)). Aliquots of 0.1 ml are removed for total counts (MARK III Liquid Scintillation Counter, Tracor Analytic) and the remainder is centrifuged at 2,100 g for 20 min at 4° C. Radioactivity is similarly measured in the resultant supernatants (0.1 ml) using a mixture of NCS and Soluscint 0 and the percentage of ($^3$H)-thymidine released is then calculated.

The effects of the four sodium salts, fluoride, chloride, thiocyanate and bicarbonate, on the bacteriolysis of *Strep. mutans* GS5 treated with lysozyme (30 ug or 75 ug/ml) and chymotrypsin (1 ug/ml) in 0.025M Hepes buffer, pH 7.3 is determined as follows: Cells are preincubated in the buffer with stirring at 37° C. After 1 hour, various concentrations of HEWL are added and incubation continued for an additional 2 hours. One milliliter of cell suspension is then placed into 15 ml polystyrene disposable centrifuge tubes (Falcon, Oxnard, Calif.) containing 100 ul of aqueous stock salt solutions such that the final salt molar concentrations are 0.03, 0.05, 0.07, 0.09 and 0.10M. Immediately upon mixing cells with salts, tubes are mixed vigorously with a Vortex mixer for 15 seconds and are then shaken at 300 rpm in a Psychrotherm G26 Incubator (New Brunswick Scientific, New Brunswick, N.J.). During the subsequent 2 hours, tubes are intermittently mixed with a Vortex mixer. At the end of the reaction period, samples are quantitated for release of ($^3$H)-thymidine as described above.

Varying concentrations of fluoride, chloride or thiocyanate (0.01 to 0.1M final molarity) are combined with fixed concentrations of bicarbonate and added to reaction mixtures containing 30 ug HEWL/ml and 1 ug trypsin/ml in MES buffer, pH 5.2. Additional experiments are carried out at the lower pH under the same conditions using either two or all three of the sodium salts in combination with bicarbonate, trypsin and HEWL. Lysis is quantitated as described above.

ASSAY RESULTS

Comparison of Effectiveness of Inorganic Anions in Cell Lysis at Neutral pH

Figure 1B:
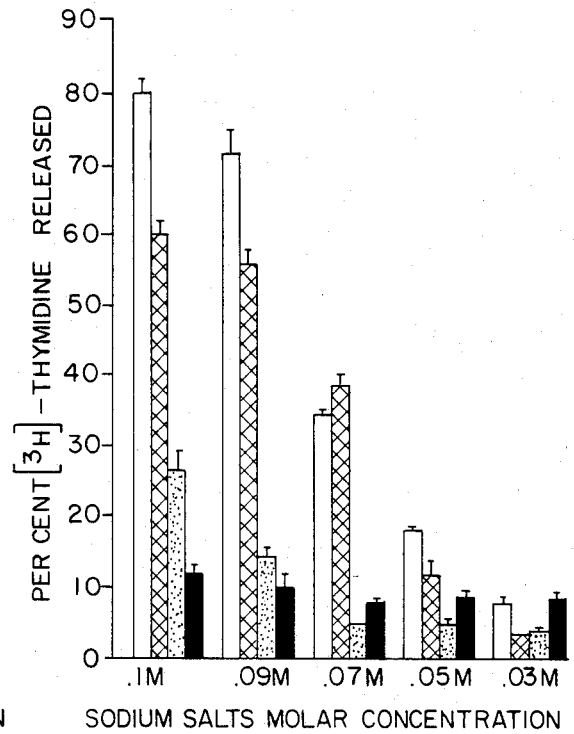
Figure 1C:
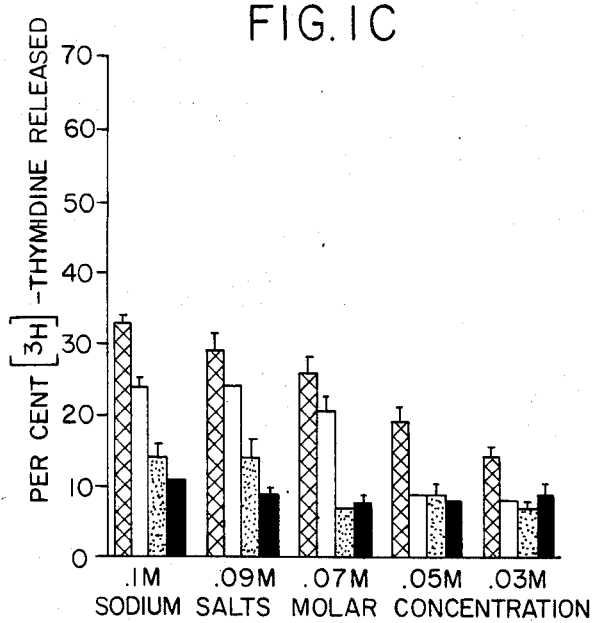

Lytic effectiveness is monotored at neutral pH at two HEWL concentrations with or without chymotrypsin. With HEWL alone, only the sodium salts of $HCO_3^-$ and $SCN^-$ are effective in promoting cell lysis as NaF and NaCl caused the release of less than 15 percent of radiolabeled thymidine which has previously been determined to be mainly pool thymidine or small molecular weight thymidine nucleotides (Goodman et al., 1981; Pollock et al., 1981; Wilkens et al., (1982). At 75 ug HEWL/ml, SCN anion appeared more effective than $HCO_3^-$ but this was not true at 30 ug HEWL/ml. At the higher lysozyme concentration, there was greater release of thymidine at the higher salt concentrations tested; however, more lysis was observed at the lower HEWL concentration at lower salt concentrations (compare FIGS. 1C to 1A for $HCO_3^-$).

Figure 1D:
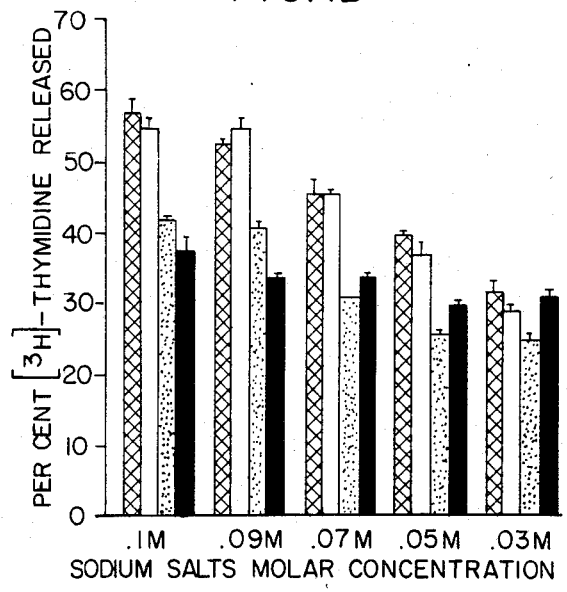

At each HEWL concentration, release of tritiated thymidine was greater in reactions containing both enzymes rather than lysozyme alone. For either the dual enzyme combination or HEWL alone, cell lysis increased as the anion concentration increases, in some cases until plateau levels were reached (see FIG. 1). At 75 ug HEWL/ml, the combination of lysozyme with chymotrypsin was particularly effective as marked changes in the lysis patterns were noted as the salt (particularly SCN and $HCO^-_3$) concentration varied. At 30 ug HEWL/ml, there was less lysis at the higher salt concentrations but more lysis at lower salt concentrations compared to 75 ug HEWL/ml (see FIGS. 1B and 1D) for the combination enzyme system. At 30 ug HEWL/ml in the presence of chymotrypsin, both chloride and fluoride exhibited lytic potency and were almost as effective as bicarbonate and thiocyanate. Control reaction mixtures or Strep. mutans GS5 treated with chymotrypsin alone were found to release approximately 15 to 20 percent or less of their tritiated thymidine lable at all salt concentrations tested.

Lysis by Bicarbonate in low pH Reaction Mixtures

Figure 2:
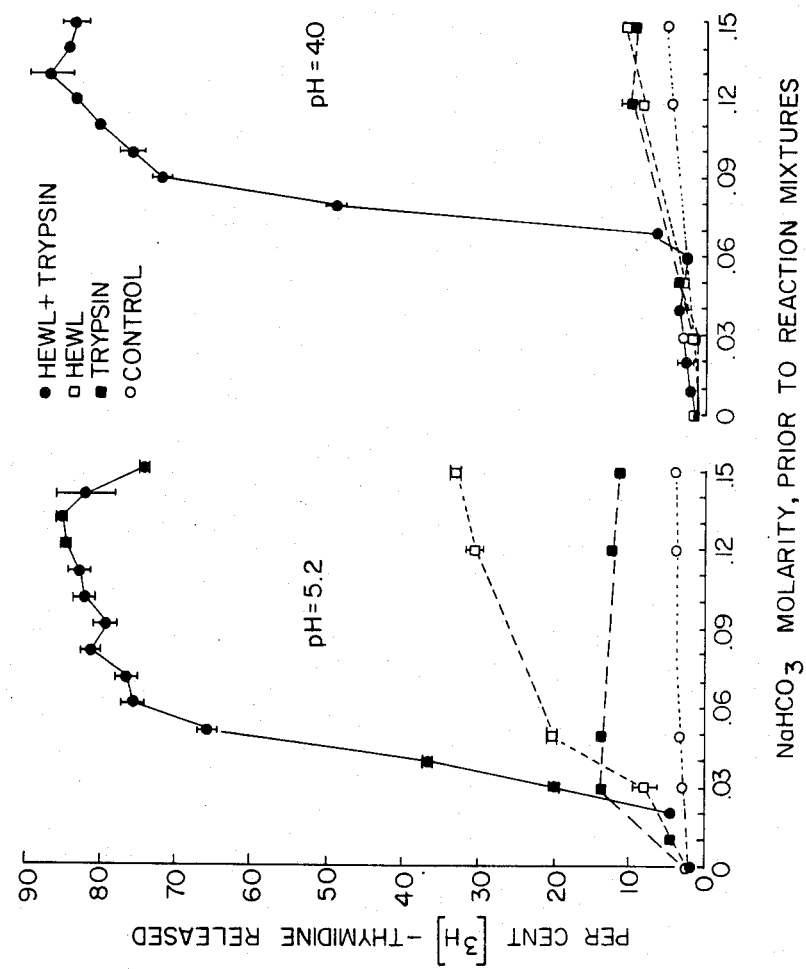
FIGS. 2 and 3 are plates of lysis at different bicarbonate levels and pHs.

In acetate buffer, pH 4.0, lysis is observed only in bicarbonate reaction mixtures containing HEWL and trypsin. (See FIG. 2) In buffer, pH 5.2, HEWL alone caused approximately 30 percent release of radiolabeled thymidine at a final molarity of 0.12M $NaHCO_3$. Comparison of the data indicated that the lysis pattern and the maximum degree of lysis are essentially the same for both pH 4.0 and 5.2 reaction mixtures except that more sodium bicarbonate has to be added at the lower pH in order to initiate the lytic process. From the Henderson-Hasselbach equation, calculations are made to determine the change in concentration of the $HCO_3$ anion upon addition of sodium bicarbonate to low pH reaction mixtures (see Table I).

TABLE I

DETERMINATION OF pH AND CALCULATION OF BICARBONATE CONCENTRATIONS IN LOW pH REACTION MIXTURES

| Buffer | Molarity of Added NaHCO$_3$ | New pH | New Molarity of HCO$_3$ |
| --- | --- | --- | --- |
| MES pH 5.2 | 0 | 5.2 | 0 |
| | .01 | 5.9 | .004 |
| | .02 | 6.2 | .012 |
| | .03 | 6.5 | .021 |
| | .04 | 6.7 | .031 |
| | .05 | 6.8 | .041 |
| | .06 | 6.9 | .051 |
| | .07 | 7.0 | .062 |
| | .08 | 7.1 | .072 |
| | .09 | 7.2 | .084 |
| | .15 | 7.6 | .140 |
| Acetate, pH 4.0 | 0 | 4.0 | 0 |
| | .01 | 4.2 | .0001 |
| | .05 | 5.0 | .004 |
| | .06 | 5.4 | .009 |
| | .07 | 5.7 | .018 |
| | .08 | 5.8 | .025 |
| | .09 | 6.0 | .038 |
| | .10 | 6.1 | .050 |
| | .11 | 6.2 | .063 |
| | .12 | 6.3 | .073 |
| | .13 | 6.4 | .086 |
| | .15 | 6.5 | .108 |

Figure 3:
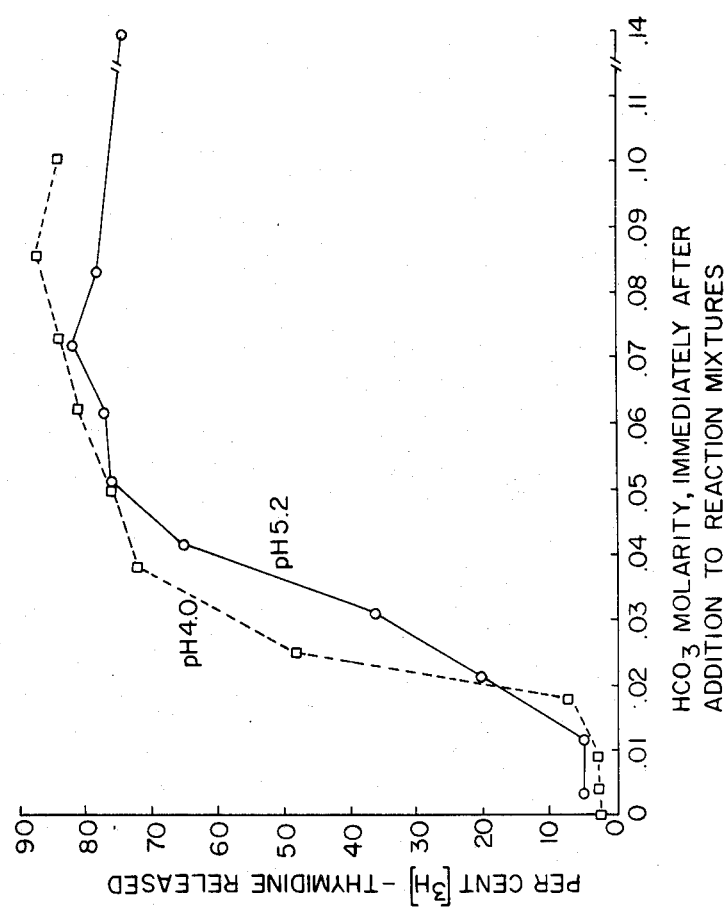

Lysis for pH 4.0 and 5.2 were found to be very similar when curves were generated by plotting release of thymidine versus the $HCO_3$ anion concentrations (see FIG. 3).

Synergism of Fluoride and Bicarbonate Anions

Figure 4:
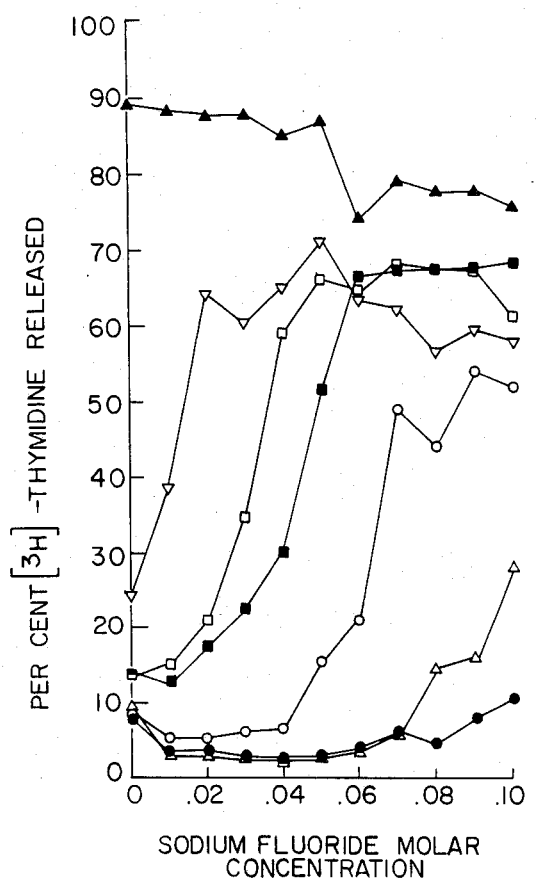
FIG. 4 is a plot of thymidine release from *S. mutans* (lysis) against concentrations of bicarbonate and fluoride.

FIG. 4 illustrates the effect obtained by combining bicarbonate and fluoride in Strep. mutans GS5 lytic studies at pH 5.2. Either in the absence or in the presence of 0.01M $NaHCO_3$, no significant lytic effect is observed at concentrations of up to 0.08M sodium fluoride. However, at 0.01M $NaHCO_3$, a concentration which in itself does not yield release of ($^3H$)-thymidine (see FIG. 2), lysis is initiated at concentrations greater than 0.08M NaF. At 0.02M $NaHCO_3$, lysis is already significant at 0.06M NaF. With increasing concentrations of bicarbonate, lysis increases with still lower fluoride concentrations. However, as the concentration of $NaHCO_3$ is further raised, the combination with fluoride causes an apparent inhibition of lysis at the higher ionic strengths. At 0.1M $NaHCO_3$, fluoride does not further enhance the near maximum amount of cell lysis observed. At each sodium bicarbonate concentration, lysis appears to plateau and the higher the bicarbonate concentration, the greater the level of the lytic response.

Lysis by Chloride or Thiocyanate in Combination with Bicarbonate

Figure 5:
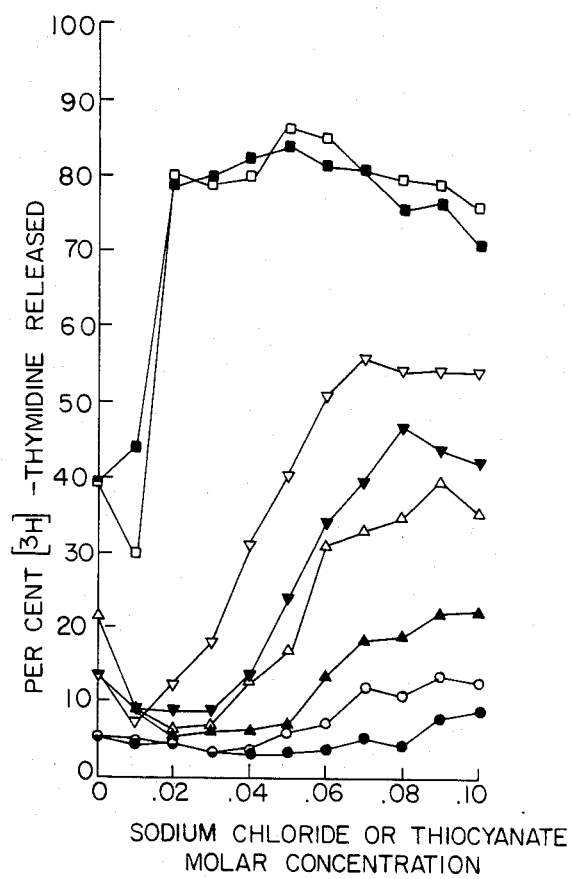
FIG. 5 is a plot of thymidine release from *S. mutans* (lysis) against concentrations of bicarbonate and chloride or thiocyanate.
Figure 7A:
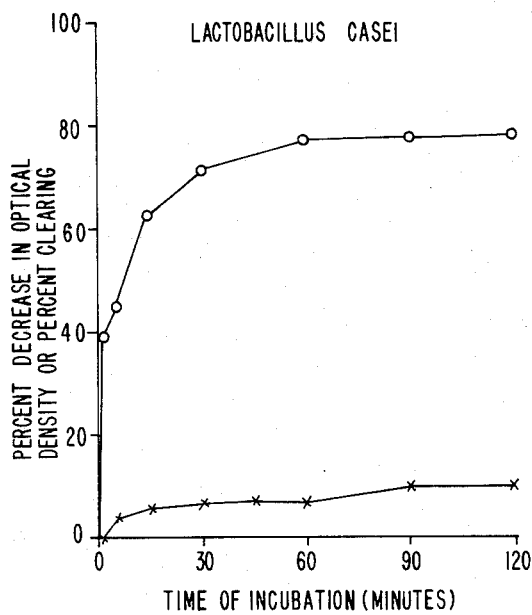
FIGS. 7 (A & D) is a series of plots of optical density (lysis of various bacteria) against incubation time for cells treated with lysozyme, trypsin and a mixture of bicarbonate/thiocyanate and chloride against lysozyme plus trypsin, but without salts.
Figure 7B:
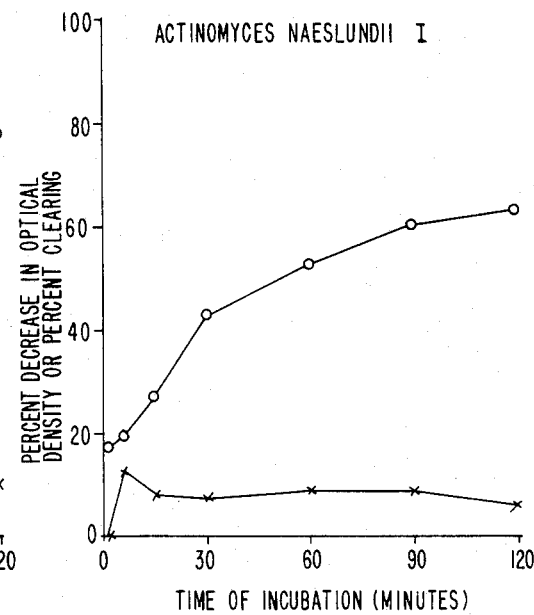
Figure 7C:
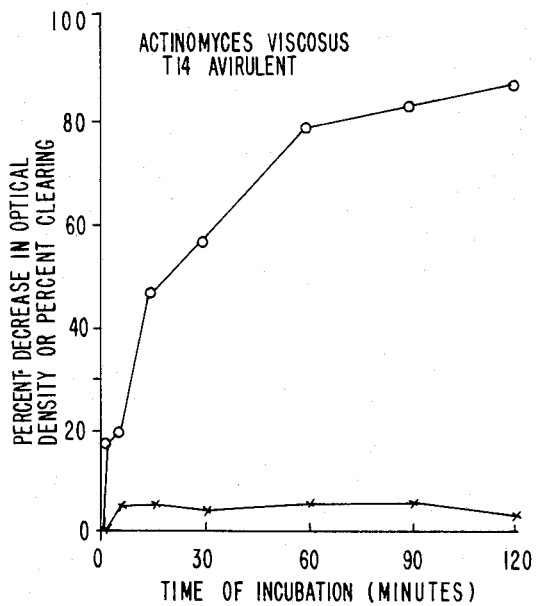
Figure 7D:
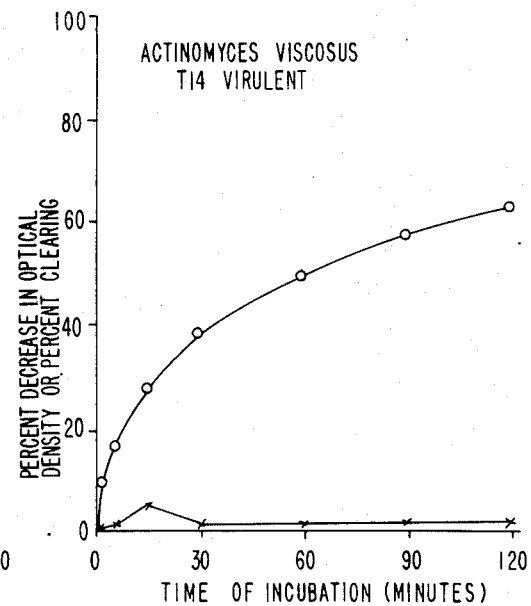

In combination with fluoride or chloride, bicarbonate appears to show differing lytic effectiveness depending on the concentration of the halide anions (see FIGS. 4 and 5). However, the lytic effect with chloride or fluoride is not as great as when bicarbonate and thiocyanate are combined and added to the pH 5.2 reaction mixtures (see FIG. 5). At concentrations of 0.01–0.02M sodium chloride or thiocyanate, an unexplained decrease in tritiated thymidine release is sometimes observed but lysis is found to increase as the anion concentration is further increased. At 0.05M $NaHCO_3$, there is a steep rise in cell lysis at either 0.02M NaSCN or NaCl (see FIG. 5) similar to that observed for NaF (see FIG. 4).

Lysis with all four Anions

At an apparent sublytic concentration of NaHCO$_3$ (0.02M), the combination with any two of 0.02M NaF, NaCl and NaSCN does not result in significant release of thymidine from the HEWL-trypsin-treated cells. When NaHCO$_3$ was combined with all three salts, however, a significant lytic effect is observed (see FIG. 6A). Increasing the concentration of F$^-$, Cl$^-$ and SCN$^-$ to 0.03M while maintaining the HCO$_3^-$ concentration at 0.02M enhances lysis dramatically (see FIG. 6B). Mixtures of bicarbonate and any two of the three sodium salts results in cell lysis greater than the lysis observed by combining any one of the three salts with bicarbonate, although the combination with NaSCN is almost as effective as a mixture of NaHCO$_3$, NaCl and NaF.

TABLE

DECREASE IN TURBIDITY OF ORAL MICROORGANISMS UPON ACTIVATION OF LYSOZYME-TRYPSIN-DAMAGED BACTERIA BY SODIUM BICARBONATE, SODIUM THIOCYANATE AND SODIUM CHLORIDE.

Optical Density (Absorption) at 675 nm[a]

| Incubation Time (Minutes)[b] | Lactobacillus casei | | Actinomyces naeslundii I | | Actinomyces viscosus Avirulent | | Actinomyces viscosus T 14 Virulent | |
|---|---|---|---|---|---|---|---|---|
| | Lysozyme + Trypsin | Lysozyme + Trypsin + Salts[c] | Lysozyme + Trypsin | Lysozyme + Trypsin + Salts | Lysozyme + Trypsin | Lysozyme + Trypsin + Salts | Lysozyme + Trypsin | Lysozyme + Trypsin + Salts |
| 0 | .335 | .310 | .222 | .208 | .299 | .296 | .227 | .244 |
| 0.5 | .335 | .188 | .222 | .171 | .299 | .243 | .227 | .222 |
| 5 | .322 | .160 | .190 | .168 | .283 | .231 | .225 | .204 |
| 15 | .318 | .101 | .204 | .142 | .279 | .151 | .216 | .176 |
| 30 | .314 | .071 | .206 | .118 | .283 | .107 | .228 | .149 |
| 60 | .310 | .052 | .201 | .099 | .281 | .064 | .238 | .123 |
| 90 | .300 | .050 | .201 | .083 | .279 | .052 | .244 | .103 |
| 120 | .299 | .047 | .207 | .073 | .289 | .039 | .237 | .092 |

Lysis Enhancement of Other Oral Cariogenic Bacteria

Bacterial cells are suspended in low ionic strength buffer at low pH (0.025 ionic strength MES buffer, pH 5.2) to simulate the conditions in the mouth at the site of a carious lesion; salts were added to yield final concentrations of bicarbonate, thiocyanate and chloride of 0.03M, 0.03M, and 0.04M, respectively, and the optical density of the suspension measured at 675 nM. The decrease in turbidity is an indicator of bacterial cell lysis. (FIG. 7, Table II).

In Vivo Elimination and Reduction of S. mutans from the Plaque of Hamsters by Treatment with Sodium Salts of Bicarbonate, Thiocyanate and Chloride The purpose of this evaluation was to determine if Streptococcus mutans colonization of the tooth surfaces of the hamster could be inhibited or reduced by the administration of solutions containing either 0.03M sodium bicarbonate or 0.03M sodium bicarbonate in combination with 0.03M sodium chloride and 0.03M sodium thiocyanate. The molar teeth of Golden Syrian Hamsters were infected with S. mutans 6715-15, a highly cariogenic strain, by brushing and by inoculation of the bacteria into the drinking water. After 30 days of colonization, a four week experiment was initiated in which control animals (no salts) were compared to those treated with either sodium bicarbonate or with all three sodium salts. No effect was observed on S. mutans colonization in either the control group or in the treatment group with sodium bicarbonate alone. However, at the end of four weeks if sodium bicarbonate was used in combination with sodium chloride and sodium thiocyanate, 50 percent of the animals has no S. mutans in their plaque while the remaining 50 percent had only minimal numbers of the organism. Moreover, already by the end of the third week, a significant reduction of S. mutans was noted in the plaque of those animals being treated with the combination of the three salts.

The following examples describe in detail formulations encompassing the compositions of the present invention. It will be apparent to those skilled in the art that many modifications, both of materials and methods, may be practiced without departing from the spirit and scope of the invention.

EXAMPLE I

MOUTH SPRAY

| | |
|---|---|
| Peppermint Spirit | 43.2 ml. |
| Saccharin Sodium | 0.07 gm. |
| Sodium bicarbonate | 0.25–3.24 gm. |
| Sodium chloride | 0.23–1.76 gm. |
| Sodium thiocyanate | 0.49–2.4 gm. |
| Water to | 300 ml |
| Can Also Add: | |
| Sodium fluoride (if desired) | 0.25–1.26 gm. |

The formulation is utilized by spraying aliquots of 0.25 to 0.50 ml. onto the gingiva and tooth surfaces of each quadrant between 1 and 3 times per day.

EXAMPLE II

MOUTHWASH FORMULATION

| | |
|---|---|
| Sodium bicarbonate | 0.84–10.8 gm. |
| Sodium chloride | 1.17–5.85 gm. |
| Sodium thiocyanate | 1.62–8.0 gm. |
| Thymol | 0.5 gm. |
| Eucalyptol | 1.0 ml. |
| Methyl salicylate | 0.5 ml. |
| Amaranth solution | 14.0 ml. |
| Alcohol | 50.0 ml. |
| Glycerin | 100.0 ml. |
| Water to | 1000.0 ml. |
| Can Also Add: | |
| Sodium fluoride (if desired) | 0.84–4.20 gm. |

The formulation is utilized by rinsing the mouth for about 30–60 seconds from 1–3 times per day with 10 to 15 ml. of undiluted wash.

EXAMPLE III

TOOTHPASTE FORMULATION

| | |
|---|---|
| Carboxymethyl cellulose 120H | 1.8 gm. |
| Glycerin | 2.0 ml. |
| Propylene glycol | 39.0 ml. |
| Purified water | 27.0 ml. |
| Methyl paraben | 0.2 gm. |
| Saccharin Sodium (50% sol.) | 0.2 ml. |
| Peppermint Oil | 0.6 ml. |
| Mineral Oil | 2.0 ml. |
| Triton X-100 | 5.0 gm |
| Silica | 1.0 gm. |
| Sodium bicarbonate | 0.08–1.08 gm. |
| Sodium chloride | 0.12–0.59 gm. |
| Sodium thiocyanate | 0.16–0.80 gm. |
| *Can Also Add:* | |
| Sodium fluoride | 0.084–0.42 gm. |

The formulation is utilized by cleaning the teeth with about 1 to 2 gm. of the paste between 1 and 3 times per day.

EXAMPLE IV

CHEWING GUM

| | Each Stick |
|---|---|
| Gum Base: | |
| Estergum | 142 mg. |
| Coumarone Resin | 213 mg. |
| Latex (dry) | 71 mg. |
| Paraffin Wax (melting pt. 180° F.) | 47 mg. |
| Sorbitol (for sugarless gum) | 1309 mg. |
| Corn Syrup (Baume 45° C.) | 400 mg. |
| Flavoring | q.s. |
| Sodium Bicarbonate | 0.2–43 mg. |
| Sodium Chloride | 0.3–23 mg. |
| Sodium Thiocyanate | 0.4–32 mg. |
| *Can Also Add:* | |
| Sodium Fluoride | 0.2–16 mg. |

The formulation is utilized as needed.

EXAMPLE V

BREATH FRESHENER TABLET

| | Each Tablet |
|---|---|
| Wintergreen Oil | 0.6 mg. |
| Talc | 10.0 mg. |
| Menthol | 0.85 mg. |
| Peppermint Oil | 0.3 mg. |
| Sodium Saccharin | 0.3 mg. |
| Mannitol USP (powdered) | 180.95 mg. |
| Sodium Stearate | 2.0 mg. |
| Sodium Bicarbonate | 0.2–43 mg. |
| Sodium Chloride | 0.3–23 mg. |
| Sodium Thiocyanate | 0.4–32 mg. |
| Sorbitol USP (powdered) | 180.0 mg. |
| Lactose USP (powdered) (q.s.) | 1 gm. |
| *Can Also Add:* | |
| Sodium Flouride | 0.2–16 mg. |

The formulation is utilized as needed.

EXAMPLE VI

CHEWABLE MULTIVITAMIN TABLET

| | Each Tablet |
|---|---|
| Vitamin A USP (dry stabilized form) | 5000 USP units |
| Vitamin D (dry stabilized form) | 400 USP units |
| Ascorbic Acid USP | 60 mg. |
| Thiamine HCl USP | 1 mg. |
| Riboflavin USP | 1.5 mg. |
| Pyridoxine HCl USP | 1 mg. |

-continued
CHEWABLE MULTIVITAMIN TABLET

| | Each Tablet |
|---|---|
| Cyanocobalamin USP | 2 ug. |
| Calcium Pantothenate USP | 3 mg. |
| Niacinamide USP (granular) | 10 mg. |
| Mannitol USP (granular) | 236.2 mg. |
| Corn Starch | 16.6 mg. |
| Sodium Saccharin | 1.1 mg. |
| Sodium Stearate | 6.6 mg. |
| Talc | 10 mg. |
| Wintergreen Oil | 1.2 mg. |
| Menthol | 1.7 mg. |
| Peppermint Oil | 0.6 mg. |
| Sodium Bicarbonate | 0.2–43 mg. |
| Sodium Chloride | 0.3–23 mg. |
| Sodium Thiocyanate | 0.4–32 mg. |
| *Can Also Add:* | |
| Sodium Fluoride | 0.2–16 mg. |

The formulation is utilized by taking one tablet each day.

EXAMPLE VII

CANDY (Lozenge)

| | Each Tablet |
|---|---|
| Acacia | as required for binding |
| Mannitol (powdered) USP | 180.0 mg. |
| Sodium Saccharin | 1.1 mg. |
| Sodium Stearate | 5.0 mg. |
| Licorice | 98 mg. |
| Talc | 10 mg |
| Capsicum | 2 mg |
| Menthol | 1.8 mg. |
| Sodium Bicarbonate | 0.2–43 mg. |
| Sodium Chloride | 0.3–23 mg. |
| Sodium Thiocyanate | 0.4–32 mg. |
| Lactose (powdered) USP (q.s.) | 2.0 gm. |
| *Can Also Add:* | |
| Sodium Fluoride | 0.2–16 mg. |

The formulation is utilized as needed.

We claim:

1. A method of inhibiting or reducing Streptococcus mutans colonization of carious lesions of tooth surfaces infected with cariogenic strains of *S. mutans* in substantially normal physiological concentrations in submandibular, parotide and mixed human salivas containing concentrations of bicarbonate ion of from about 1 to about 60 mM., chloride ion from about 10 to about 50 mM., and thiocyanate ion from about 0.5 to 4.5 mM., said concentrations being ineffective to kill bacteria, which comprises:

treating between one and three times a day the sites of caries lesions on said teeth with about 0.03M sodium bicarbonate by weight used in combination with about 0.03M. sodium chloride, and 0.03M. sodium thiocyanate at least until the significant reduction of *S. mutans* can be noted.

2. A fluoride free dentrifice consisting essentially of between about 0.1% and 1.75% by weight bicarbonate ion, between about 0.15 and 0.7% by weight of chloride ion and between about 0.2 and 1% by weight of thiocyanate ion in combination with a pharmaceutically acceptable cation as the pharmacological active ingredients.

3. A fluoride free dentrifice in accordance with claim 2 formulated into a tooth paste.

4. A dentrifice consisting essentially of between about 0.1 and 0.5% by weight of sodium fluoride, between about 0.1% and 1.75% by weight bicarbonate ion, between about 0.15 and 0.7% by weight of chloride ion and between about 0.2 and 1% by weight of thiocyanate ion in combination with a pharmaceutically acceptable cation as the pharmacological active ingredients.

5. A dentrifice in accordance with claim 4 formulated in a tooth paste.

* * * * *